United States Patent
Metcalf

(10) Patent No.: US 7,056,312 B1
(45) Date of Patent: Jun. 6, 2006

(54) SANITARY NAPKIN WITH ABSORBENT TAB

(76) Inventor: Regina L. Metcalf, 3314 Sun Valley, Shreveport, LA (US) 71109

( * ) Notice: Subject to any disclaimer, the term of this patent is extended or adjusted under 35 U.S.C. 154(b) by 128 days.

(21) Appl. No.: 10/463,477

(22) Filed: Jun. 17, 2003

(51) Int. Cl.
*A61F 13/15* (2006.01)

(52) U.S. Cl. .................. 604/385.101; 604/385.01; 604/385.04; 604/385.28

(58) Field of Classification Search ........... 604/385.01, 604/385.17, 385.101, 378, 385.13, 385.04, 604/385.28
See application file for complete search history.

(56) References Cited

U.S. PATENT DOCUMENTS

| | | | |
|---|---|---|---|
| 4,072,150 A | * | 2/1978 | Glassman .................. 604/389 |
| 5,743,896 A | * | 4/1998 | Parker .................. 604/385.01 |
| 6,241,714 B1 | | 6/2001 | Raidel et al. ................ 604/378 |
| 6,296,628 B1 | | 10/2001 | Mizutani ..................... 604/387 |
| 6,348,047 B1 | | 2/2002 | Harper .................. 604/385.17 |
| 6,465,711 B1 | | 10/2002 | Brisbois ..................... 604/378 |
| 6,471,682 B1 | | 10/2002 | Kashiwag .............. 604/385.27 |
| 6,475,199 B1 | | 11/2002 | Gann et al. ............ 604/385.01 |
| 6,508,795 B1 | | 1/2003 | Samuelsson et al. ........ 604/378 |

* cited by examiner

*Primary Examiner*—Jacqueline F. Stephens
(74) *Attorney, Agent, or Firm*—R. Keith Harrison

(57) ABSTRACT

A new and improved sanitary napkin that prevents backflow of menstrual fluids from the napkin during use. The sanitary napkin includes a napkin body having an absorbent tab that extends from the absorbent surface of the napkin body. In use, the absorbent tab blocks and absorbs menstrual fluid and prevents the fluid from running off the back edge or end of the napkin body.

26 Claims, 1 Drawing Sheet

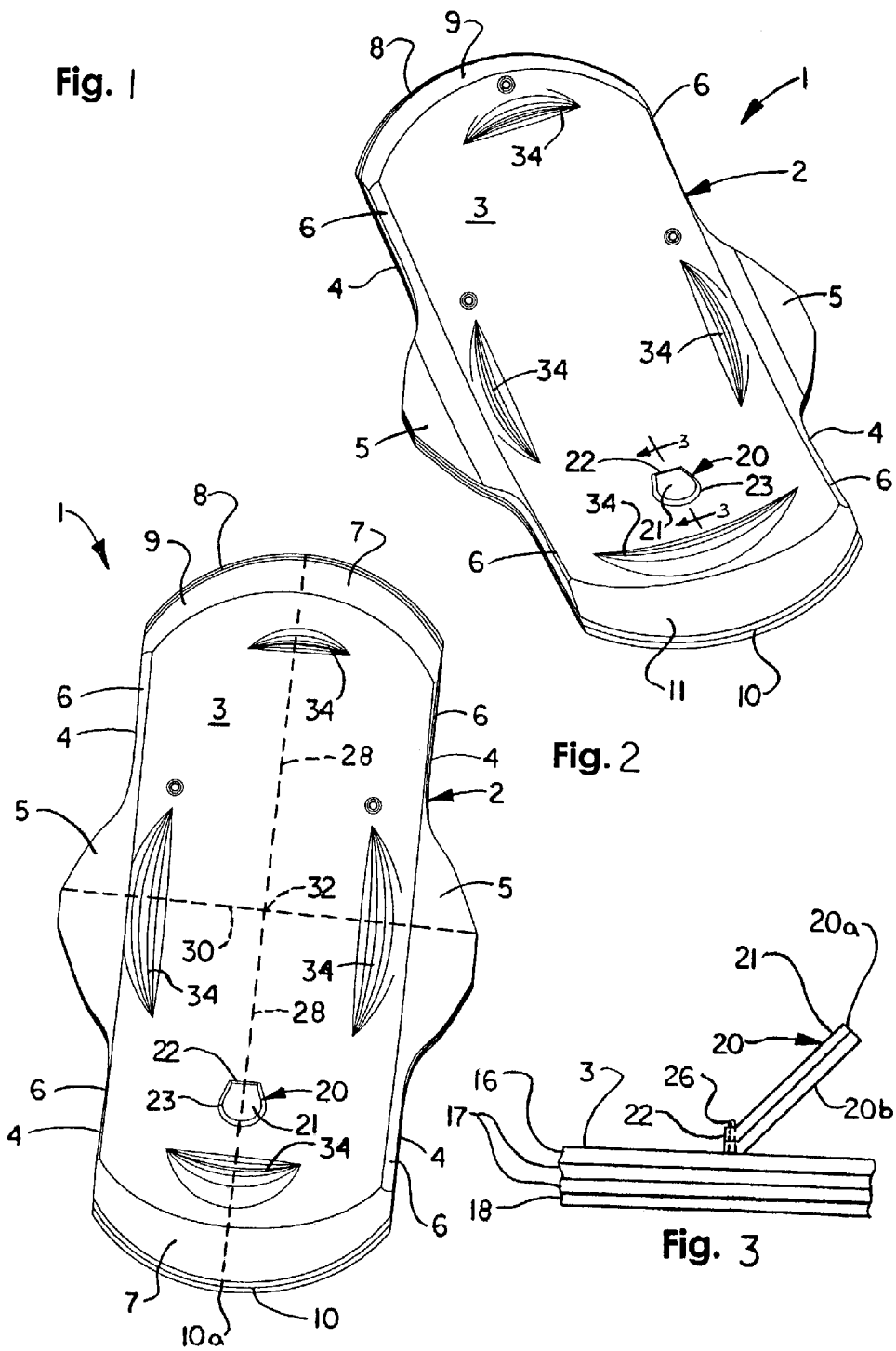

SANITARY NAPKIN WITH ABSORBENT TAB

FIELD OF THE INVENTION

The present invention relates to sanitary napkins used to absorb and retain menstrual fluids. More particularly, the present invention relates to a sanitary napkin having an absorbent tab that prevents backflow of menstrual fluids from the napkin during use.

BACKGROUND OF THE INVENTION

A variety of sanitary napkins are known in the art for absorbing menstrual fluids during a female wearer's menstrual period to prevent soiling of the wearer's undergarment and/or overgarment. Sanitary napkins are typically constructed as multi-layered sheets of laminated absorbent material and are worn between the wearer's undergarment and genital area on the outside of the body. Sanitary napkins typically both absorb the menstrual flow and block flow of the menstrual fluids onto the wearer's clothing.

One of the drawbacks of typical conventional sanitary napkins is that the napkins fail to adequately prevent backflow of menstrual fluids from the rear edge of the napkin as the napkin is used by a wearer, particularly when the wearer sits on a surface. This frequently results in soiling of the wearer's undergarment and/or overgarment.

Various sanitary napkins or absorbent articles are disclosed in U.S. Pat. Nos. 6,241,714; 6,296,628; 6,348,047; 6,475,199; 6,471,682; 6,465,711; and 6,508,795.

SUMMARY OF THE INVENTION

The present invention is generally directed to a new and improved sanitary napkin that prevents backflow of menstrual fluids from the napkin during use. The sanitary napkin includes a napkin body having an absorbent tab that extends from the absorbent surface of the napkin body. In use, the absorbent tab blocks and absorbs menstrual fluid and prevents the fluid from running off the back edge or end of the napkin body.

BRIEF DESCRIPTION OF THE DRAWINGS

The invention will be better understood by reference to the accompanying drawings, in which:

FIG. 1 is a perspective view of an illustrative embodiment of the sanitary napkin with absorbent tab of the present invention;

FIG. 2 is a top view of the sanitary napkin with absorbent tab; and

FIG. 3 is a cross-sectional view, taken along section lines 3—3 in FIG. 1, of the absorbent tab element of the sanitary napkin with absorbent tab.

DESCRIPTION OF THE PREFERRED EMBODIMENTS

Referring to FIGS. 1–3 of the drawing, an illustrative embodiment of the sanitary napkin with absorbent tab, hereinafter napkin, of the present invention is generally indicated by reference numeral 1. The napkin 1 includes an elongated napkin body 2 which as shown in FIG. 3 may be constructed of an upper layer 16, one or more middle layers 17 and a bottom layer 18. At least one of the upper layer 16, the middle layer or layers 17 and the bottom layer 18 is typically cotton or other material or laminate which is capable of absorbing and retaining moisture, and one or more of the layers may be a barrier layer including a liquid-impervious material such as plastic. The upper layer 16 has an upper, absorbent surface 3 which, in use, faces the vaginal opening (not shown) of a wearer. The absorbent surface 3 typically has multiple creases 34.

The napkin body 2 typically has a generally elongated configuration, as shown, and includes a front end 8 spaced from a rear end 10. The front end 8 and rear end 10 may each have a generally curved or arcuate configuration, as shown. An absorbent front wall 9 and an absorbent rear wall 11, each extending beyond the plane of the absorbent surface 3, may define the front end 8 and the rear end 10, respectively, of the napkin body 2. Absorbent side walls 6 that are typically continuous with the front end wall 9 and the rear end wall 11 may extend beyond the plane of the absorbent surface 3 and define lateral edges 4 of the napkin body 2. A "wing" or lateral tab 5 may extend from each lateral edge 4 of the napkin body 2 for folding under and engaging the undergarment (not shown) of the wearer to secure the napkin body 2 onto the undergarment, typically in conventional fashion.

It is understood that the foregoing description of the napkin body 2 represents only one example of a sanitary napkin which is suitable for purposes of the present invention, and the napkin body 2 may have characteristics and features which depart from those heretofore described. For example, an adhesive (not shown) may be provided on the bottom layer 18 of the napkin body 2, alone or in combination with the lateral tabs 5, to facilitate attachment of the napkin body 2 to the undergarment of a wearer. Other techniques known by those skilled in the art may be used to secure the napkin body 2 onto the wearer's undergarments. Furthermore, the napkin body 2 may have any suitable moisture-absorbing, retaining and/or barrier construction that varies from the upper layer 16, the middle layer or layers 17 and the bottom layer 18 construction heretofore described with respect to FIG. 3.

As shown in FIG. 2, the napkin body 2 may be divided into four quadrants of equal size by an imaginary longitudinal center line 28 and an imaginary transverse center line 30 which intersect each other at a center point 32. The longitudinal center line 28 divides the napkin body 2 into left and right halves of substantially equal size, whereas the transverse center line 30 divides the napkin body 2 into front and rear halves of substantially equal size. An absorbent tab 20 extends from the absorbent surface 3. As shown in FIG. 3, the absorbent tab 20 typically has a generally planar configuration and may have a laminated bi-layered construction with a front tab layer 20a and a rear tab layer 20b. Alternatively, the absorbent tab 20 may be non-planar and have a single-layered construction or a multi-layered construction with any desired number of layers. The front tab layer 20a is typically an absorbent material or laminate such as cotton, for example, and the rear tab layer 20b is typically a barrier material such as plastic, for example, which is substantially impervious to liquids. However, the absorbent tab 20 may have any number of absorbent layers or absorbent and barrier layers arranged in any desired sequence. The width of the absorbent tab 20 is disposed generally perpendicular to flow of menstrual fluids toward the rear end 10 of the napkin body 2, in use of the napkin 1 as hereinafter described. The front tab layer 20a has an absorbent surface 21 that faces the front end 8 of the napkin body 2. The absorbent tab 20 further includes a front or bottom attachment edge 22 which is attached to the absorbent surface 3 typically by stitching 26, as shown in FIG. 3, and a typically elliptical raised edge 23 which defines the perimeter of the absorbent tab 20. Rather than being stitched to the absorbent surface 3, the absorbent tab 20 may alternatively be formed in one piece with the upper layer 16, with the middle layer or layers 17 or with the bottom layer 18 of the napkin body 2, or may be attached to the napkin body 2 according to other techniques known by those skilled in the art. In addition, the raised edge 23 of the absorbent tab 20 may define a generally rectangular or any other desired shape.

In a typical embodiment, the absorbent tab 20 is attached to or extends from or beyond the absorbent surface 3 at a location which is from about halfway between the center point 32 and the rearmost portion 10a of the rear end 10 to typically about 25% of the total distance between the center point 32 and the rearmost portion 10a closer to the rearmost portion 10a than to the center point 32. Preferably, the absorbent tab 20 is about halfway between the center point 32 and the rearmost portion 10a of the rear end 10, as shown in FIG. 2. The width of the attachment edge 22 of the absorbent tab 20 is typically about 1–2 inches, and the attachment edge 22 extends parallel to the transverse center line 30 and transverse to the longitudinal center line 28. Accordingly, the attachment edge 22 extends from typically about ½ inch to about 1 inch on each side of the longitudinal center line 28.

In use, the napkin body 2 of the napkin 1 is secured to the undergarment (not shown) of a female wearer and the undergarment is donned by the wearer with the absorbent surface 3 of the napkin body 2 facing the wearer's vaginal opening (not shown). The absorbent tab 20 is located to the rear of the vaginal opening. As the napkin body 2 absorbs menstrual fluid from the vaginal opening, some of the menstrual fluid tends to flow rearwardly on the absorbent surface 3 and toward the absorbent tab 20, particularly when the wearer is in a sitting position. Accordingly, the menstrual fluid contacts the absorbent surface 21 of the absorbent tab 20, which absorbs and retains the fluid. The rear tab layer 20b is typically impervious to the menstrual fluid and acts as a barrier to block flow of the fluid through the absorbent tab 20 and toward the rear end 10 of the napkin body 2. Thus, the absorbent tab 20 prevents the menstrual fluid from running off the rear end 10 of the napkin body 2 and soiling the undergarment and/or overgarment of the wearer, particularly when the wearer is in a sitting position.

While the preferred embodiments of the invention have been described above, it will be recognized and understood that various modifications can be made in the invention and the appended claims are intended to cover all such modifications which may fall within the spirit and scope of the invention.

Having described my invention with the particularity set forth above, I claim:

1. A sanitary napkin comprising:
    a napkin body having a front end, a rear end and a center point between said front end and said rear end and having an upper liquid pervious layer; and
    an absorbent tab attached to said upper liquid pervious layer of said napkin body between said center point and said rear end, said absorbent tab having an absorbent surface disposed at an obtuse angle with respect to said napkin body.

2. The sanitary napkin of claim 1 wherein said absorbent tab comprises cotton.

3. The sanitary napkin of claim 1 wherein said absorbent tab comprises at least one liquid-absorbent layer and at least one liquid-impervious layer.

4. The sanitary napkin of claim 3 wherein said at least one liquid-absorbent layer of said absorbent tab comprises cotton.

5. The sanitary napkin of claim 1 wherein said absorbent tab comprises a front tab layer and a rear tab layer.

6. The sanitary napkin of claim 5 wherein at least one of said front tab layer and said rear tab layer of said absorbent tab comprises cotton.

7. The sanitary napkin of claim 5 wherein said front tab layer comprises a liquid-absorbing layer and said rear tab layer comprises a liquid-impervious layer.

8. The sanitary napkin of claim 7 wherein said front tab layer of said absorbent tab comprises cotton.

9. The sanitary napkin of claim 1 wherein said absorbent tab is closer to said rear end than to said center point.

10. The sanitary napkin of claim 9 wherein said absorbent tab comprises cotton.

11. The sanitary napkin of claim 9 wherein said absorbent tab comprises a front tab layer and a rear tab layer.

12. The sanitary napkin of claim 9 wherein said absorbent tab comprises at least one liquid-absorbent layer and at least one liquid-impervious layer.

13. A sanitary napkin comprising:
    a napkin body having a front end, a rear end and a center point between said front end and said rear end and having an upper liquid pervious layer; and
    an absorbent tab attached to said upper liquid pervious layer of said napkin body about halfway between said center point and said rear end, said absorbent tab having an absorbent surface disposed at an obtuse angle with respect to said napkin body and a rear surface spaced-apart from said napkin body.

14. The sanitary napkin of claim 13 wherein said absorbent tab comprises at least one liquid-absorbent layer and at least one liquid-impervious layer.

15. The sanitary napkin of claim 13 wherein said absorbent tab comprises cotton.

16. The sanitary napkin of claim 13 wherein said absorbent tab comprises a front tab layer and a rear tab layer, with at least said front tab layer comprising a liquid-absorbent material.

17. A sanitary napkin comprising:
    a napkin body having a front end, a rear end and a center point between said front end and said rear end and having an upper liquid pervious layer; and
    a generally planar, multi-layered absorbent tab attached to said upper liquid pervious layer of said napkin body about halfway between said center point and said rear end, said absorbent tab having an absorbent surface disposed at an obtuse angle with respect to said napkin body and a rear surface disposed at an acute angle with respect to said napkin body.

18. The sanitary napkin of claim 17 wherein said absorbent tab comprises cotton.

19. The sanitary napkin of claim 17 wherein said absorbent tab comprises a front tab layer and a rear tab layer.

20. The sanitary napkin of claim 19 wherein said front tab layer comprises a liquid-absorbent material and said rear tab layer comprises a liquid-impervious layer.

21. A sanitary napkin comprising:
    a napkin body having lateral edges, a front end, a rear end and a center point between said front end and said rear end and having an upper liquid pervious layer; and
    a generally planar, multi-layered absorbent tab attached to said upper liquid pervious layer of said napkin body about halfway between said center point and said rear end and about equidistant between said lateral edges, said absorbent tab having an absorbent surface disposed at an obtuse angle with respect to said napkin body and a rear surface raised and disposed at an acute angle with respect to said napkin body.

22. The sanitary napkin of claim 21 wherein said absorbent tab comprises a front tab layer and a rear tab layer.

23. The sanitary napkin of claim 22 wherein said front tab layer comprises a liquid-absorbent material and said rear tab layer comprises a liquid-impervious material.

24. A sanitary napkin comprising:
a napkin body having a front end and a rear end, said napkin body divisible by a longitudinal center line and a transverse center line intersecting at a center point and having an upper liquid pervious layer; and
an absorbent tab attached to said upper liquid pervious layer of said napkin body about halfway between said center point and said rear end and substantially centered on said longitudinal center line, said absorbent tab disposed in a plane generally parallel to said transverse center line, said absorbent tab having a front attachment edge attached to said upper liquid pervious layer of said napkin body and a rear edge raised with respect to said napkin body; an absorbent surface disposed at an obtuse angle with respect to said napkin body; and a rear surface raised and disposed at an acute angle with respect to said napkin body.

25. The sanitary napkin of claim 24 wherein said absorbent tab comprises a front tab layer and a rear tab layer.

26. The sanitary napkin of claim 25 wherein said front tab layer comprises a liquid-absorbent material and said rear tab layer comprises a liquid-impervious material.

* * * * *